US00PP21686P2

(12) United States Plant Patent
Laurent

(10) Patent No.: US PP21,686 P2
(45) Date of Patent: Feb. 1, 2011

(54) ***VIBURNUM* PLANT NAMED 'LE BOIS MARQUIS'**

(50) Latin Name: *Viburnum odoratissimum×(Viburnum×hillier)*
Varietal Denomination: Le Bois Marquis

(75) Inventor: Maurice Laurent, Saint Romain En Gal (FR)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/584,123

(22) Filed: Aug. 31, 2009

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

UPOV-ROM GTITM, Plant Variety Database 2010/03, GTI Jouve Retrieval Software, Citation for *Viburnum* 'Le Bois Marquis' one page.*

* cited by examiner

*Primary Examiner*—June Hwu
(74) *Attorney, Agent, or Firm*—C. A. Whealy

(57) ABSTRACT

A new and distinct cultivar of *Viburnum* plant named 'Le Bois Marquis', characterized by its compact, upright and outwardly spreading plant habit; vigorous growth habit; freely branching habit; developing leaves that are bronze in color; glossy dark green-colored leaves that become reddish in color during the autumn; and good garden performance.

4 Drawing Sheets

Botanical designation: *Viburnum odoratissimum×(Viburnum×hillier)*.

Cultivar denomination: 'LE BOIS MARQUIS'.

BACKGROUND OF THE INVENTION

The present invention relates to a new and distinct cultivar of *Viburnum* plant, botanically known as *Viburnum odoratissimum×(Viburnum×hillier)* and hereinafter referred to by the name 'Le Bois Marquis'.

The new *Viburnum* plant is a product of a planned breeding program conducted by the Inventor in Saint Romain en Gal, France. The objective of the breeding program is to develop new compact *Viburnum* cultivars with attractive foliage coloration.

The new *Viburnum* plant originated from a cross-pollination in 1999 of an unnamed selection of *Viburnum odoratissimum* var. Awabuki, not patented, as the female, or seed, parent with *Viburnum×hillieri* 'Winton', not patented, as the male, or pollen, parent. The new *Viburnum* plant was discovered and selected by the Inventor in 2000 as a single flowering plant within the progeny of the stated cross-pollination in a controlled environment in Saint Romain en Gal, France.

Asexual reproduction of the new *Viburnum* plant by cuttings in a controlled environment in Beaufort en Vallee, France since June, 2004 has shown that the unique features of this new *Viburnum* plant are stable and reproduced true to type in successive generations of asexual reproduction.

SUMMARY OF THE INVENTION

Plants of the new *Viburnum* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Le Bois Marquis'. These characteristics in combination distinguish 'Le Bois Marquis' as a new and distinct cultivar of *Viburnum:*

1. Compact, upright and outwardly spreading plant habit.
2. Vigorous growth habit.
3. Freely branching habit.
4. Developing leaves that are bronze in color.
5. Glossy dark green-colored leaves that become reddish in color during the autumn.
6. Good garden performance.

Plants of the new *Viburnum* can be compared to plants of the female parent selection. Plants of the new *Viburnum* differ from plants of the female parent selection in the following characteristics:

1. Plants of the new *Viburnum* have smaller and smoother leaves than plants of the female parent selection.
2. Plants of the new *Viburnum* and the female parent selection differ in developing leaf color as plants of the female parent selection have green-colored developing leaves.
3. Leaves of plants of the new *Viburnum* have senate margins whereas leaves of plants of the female parent selection have entire margins.

Plants of the new *Viburnum* can be compared to plants of the male parent. 'Winton'. Plants of the new *Viburnum* differ from plants of 'Winton' in the following characteristics:

1. Plants of the new *Viburnum* are evergreen whereas plants of 'Winton' are deciduous.
2. Plants of the new *Viburnum* have larger and smoother leaves than plants of 'Winton'.
3. Plants of the new *Viburnum* and 'Winton' differ in developing leaf color as plants of 'Winton' have purple-colored developing leaves.

Plants of the new *Viburnum* can be compared to plants of the *Viburnum odoratissimum* 'Emerald Lustre', not patented.

Plants of the new *Viburnum* differ from plants of 'Emerald Lustre' in the following characteristics:

1. Plants of the new *Viburnum* are not as vigorous as plants of 'Emerald Lustre'.
2. Plants of the new *Viburnum* are more upright than plants of 'Emerald Lustre'.
3. Plants of the new *Viburnum* have shorter leaves than plants of 'Emerald Lustre'.
4. Plants of the new *Viburnum* and 'Emerald Lustre' differ in autumn leaf color as plants of 'Emerald Lustre' have green-colored leaves during the autumn.

BRIEF DESCRIPTION OF THE PHOTOGRAPHS

The accompanying colored photographs illustrate the overall appearance of the new *Viburnum* plant, showing the colors as true as it is reasonably possible to obtain in colored reproductions of this type. Colors in the photographs may differ slightly from the color values cited in the detailed botanical description which accurately describe the colors of the new *Viburnum* plant.

The photograph on the first sheet is a side perspective view of a typical plant of 'Le Bois Marquis' grown in a container.

The photograph on the second sheet is a close-up view of typical leaves of 'Le Bois Marquis'.

The photograph on the third sheet is a close-up view of typical leaves of 'Le Bois Marquis' during the autumn.

The photograph on the fourth sheet is a close-up view of typical flowers of 'Le Bois Marquis'.

DETAILED BOTANICAL DESCRIPTION

The aforementioned photographs and following observations, measurements and values describe plants of the new *Viburnum* grown in one-gallon containers in Grand Haven, Mich. in an outdoor nursery and under conditions which closely approximate commercial production. Plants were two years old when the photographs and the description were taken. In the description, color references are made to The Royal Horticultural Society Colour Chart, 1995 Edition, except where general terms of ordinary dictionary significance are used.

Botanical classification: *Viburnum odoratissimum*×(*Viburnum*×*hillier*) 'Le Bois Marquis'.

Parentage:

*Female, or seed, parent.*—Unnamed selection of *Viburnum odoratissimum* var. Awabuki, not patented.

*Male, or pollen, parent.*—*Viburnum*×*hillieri* 'Winton', not patented.

Propagation:

*Type.*—By cuttings.

*Time to initiate roots.*—About two months at 20° C.

*Time to produce a rooted young plant.*—About four months at 18° C.

*Root description.*—Thick, fibrous; white in color.

*Rooting habit.*—Freely branching; moderately dense.

Plant description:

*Plant form and growth habit.*—Evergreen perennial shrub; compact, upright and outwardly spreading plant habit; vigorous growth habit.

*Branching habit.*—Freely branching habit with about twelve primary lateral branches; pinching (removal of terminal apices) will enhance lateral branch development.

*Plant height.*—About 30 cm.

*Plant diameter* (*area of spread*).—About 20 cm.

Lateral branch description:

*Length.*—About 27 cm.

*Diameter.*—About 4 mm.

*Internode length.*—About 5.5 cm.

*Texture.*—Smooth, glabrous.

*Strength.*—Strong.

*Aspect.*—Upright to about 45° from vertical.

*Color, developing.*—Close to 146A.

*Color, developed.*—Close to 183A.

Foliage description:

*Arrangement.*—Opposite, simple.

*Length.*—About 11 cm.

*Width.*—About 4 cm.

*Shape.*—Elliptic.

*Apex.*—Acute to acuminate.

*Base.*—Cuneate.

*Margin.*—Serrate.

*Texture, upper and lower surfaces.*—Smooth, glabrous.

*Luster.*—Glossy.

*Venation pattern.*—Pinnate.

*Color.*—Developing leaves, upper surface: Close to 176A. Developing leaves, lower surface: Close to 186C. Fully expanded leaves, upper surface: Close to 147A; venation, close to 186D; during the autumn, color becoming closer to 59C. Fully expanded leaves, lower surface: Close to 186C; venation, close to 58A.

*Petiole.*—Length: About 1.1 cm. Diameter: About 2.5 mm. Texture, upper and lower surfaces: Smooth, glabrous. Color, upper and lower surfaces: Close to 58A.

Flower description:

*Flower appearance/arrangement.*—Single salverform flowers arranged in panicles; freely flowering habit with usually about 87 flowers per inflorescence; flowers face upright to outwardly.

*Natural flowering season.*—Continuous flowering from the late spring to early summer in Grand Haven, Mich.; flowers last about three to five weeks on the plant.

*Fragrance.*—Slightly fragrant; sweet, pleasant.

*Inflorescence height.*—About 9 cm.

*Inflorescence diameter.*—About 8 cm.

*Flower diameter.*—About 7 mm.

*Flower length* (*height*).—About 5 mm.

*Flower bud.*—Length: About 5 mm. Diameter: About 3.5 mm. Shape: Obovate. Color: Close to 155D.

*Petals.*—Quantity per flower: Single whorl of five. Length: About 3 mm. Width: About 3 mm. Shape: Obovate. Apex: Obtuse. Margin: Entire. Texture, upper and lower surfaces: Smooth, glabrous. Color: When opening, upper and lower surfaces: Close to 155D. Fully opened, upper and lower surfaced: Close to 155D.

*Sepals.*—Quantity per flower: Single whorl of five. Length: About 1 mm to 2 mm. Width: About 1.5 mm. Shape: Roughly deltoid. Apex: Acute. Margin: Entire. Texture, upper and lower surfaces: Smooth, glabrous. Color: When opening, upper and lower surfaces: Close to 146D. Fully opened, upper and lower surfaces: Close to 146D.

*Peduncles.*—Length: About 8 cm. Diameter: About 2.5 mm. Strength: Strong. Texture: Smooth, glabrous. Color: Close to 146D.

*Pedicels.*—Length: About 2 mm. Diameter: About 1.5 mm. Strength: Strong. Texture: Smooth, glabrous. Color: Close to 146D.

*Reproductive organs.*—Androecium: Quantity per flower: About five. Anther shape.: Oval. Anther size: About 1 mm by 1.5 mm. Anther color: Close to 60C. Amount of pollen: Moderate. Pollen color: Close to 201B. Gynoecium: Quantity per flower: One. Pistil length: About 3 mm. Style length: About 0.5 mm to 1 mm. Style color: Close to 146D. Stigma shape: Rounded. Stigma color: Close to 146D. Ovary color: Close to 146D.

*Seeds/fruits.*—Seed and fruit development have not been observed on plants of the new *Viburnum.*

Garden performance: Plants of the new *Viburnum* have been observed to have good garden performance and to tolerate rain, wind and temperatures ranging from about −15° C. to about 35° C.

Pathogen/pest resistance: Plants of the new *Viburnum* have not been observed to be resistant to pathogens and pests common to *Viburnum.*

It is claimed:

1. A new and distinct *Viburnum* plant named 'Le Bois Marquis' as illustrated and described.

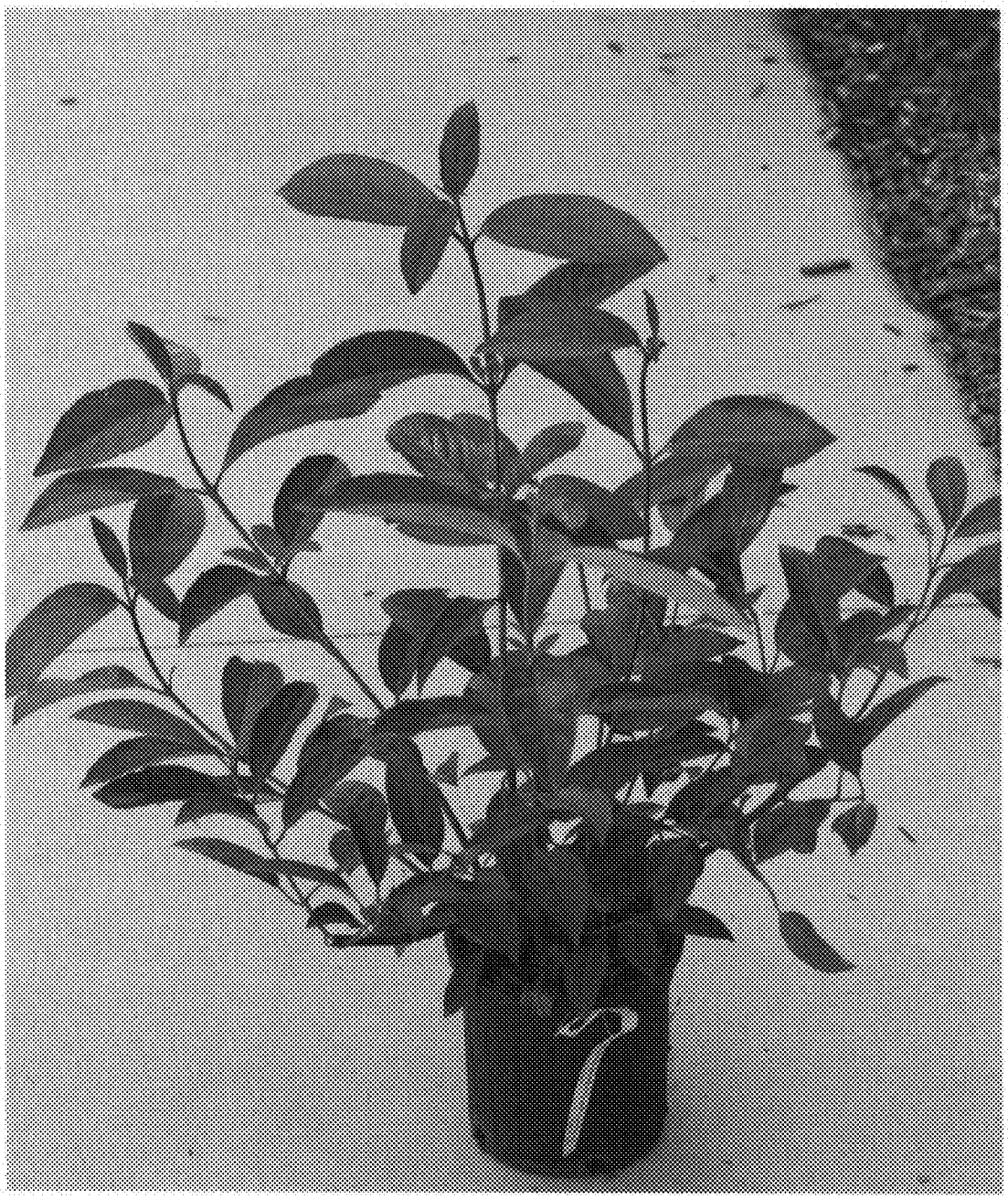

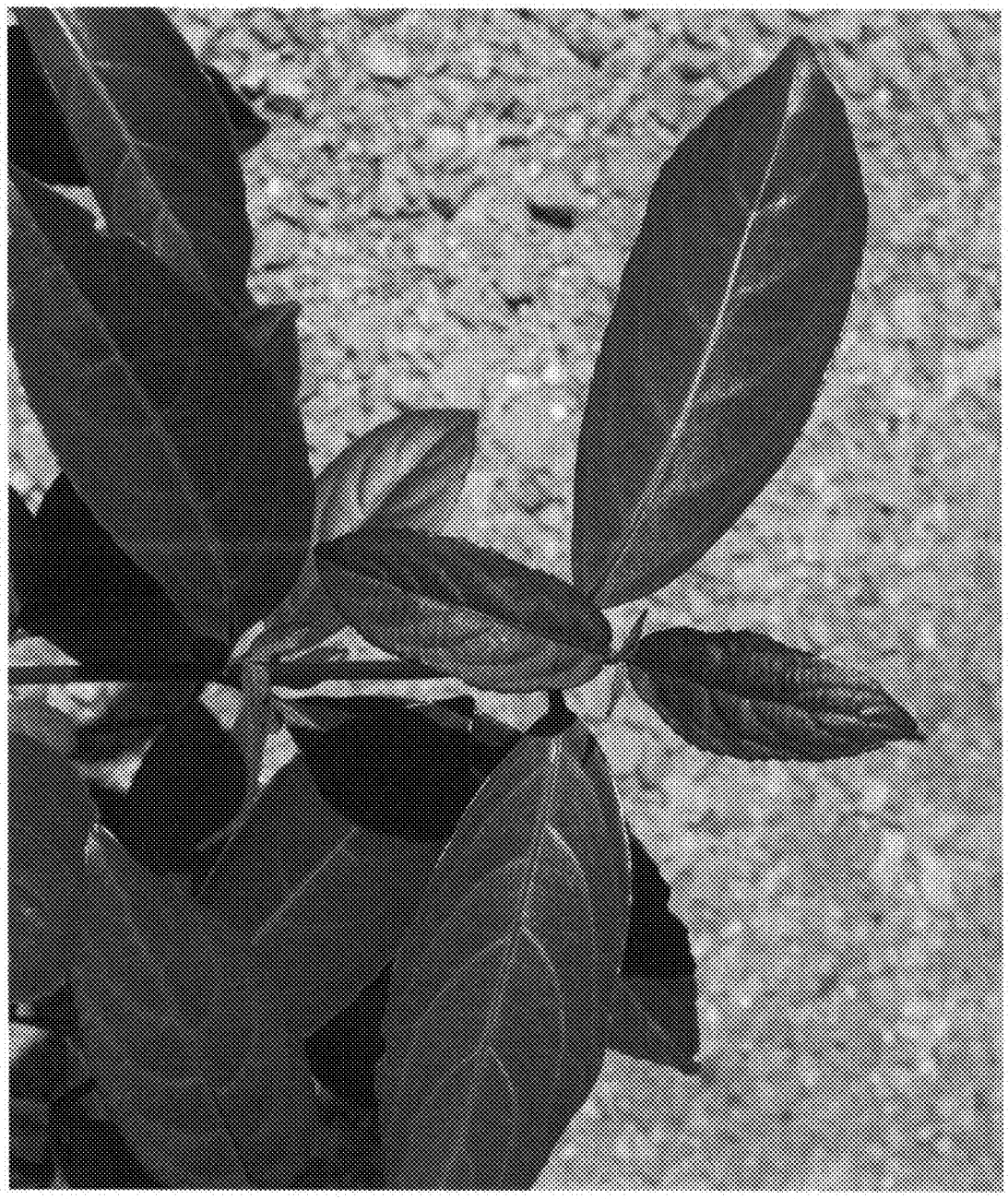

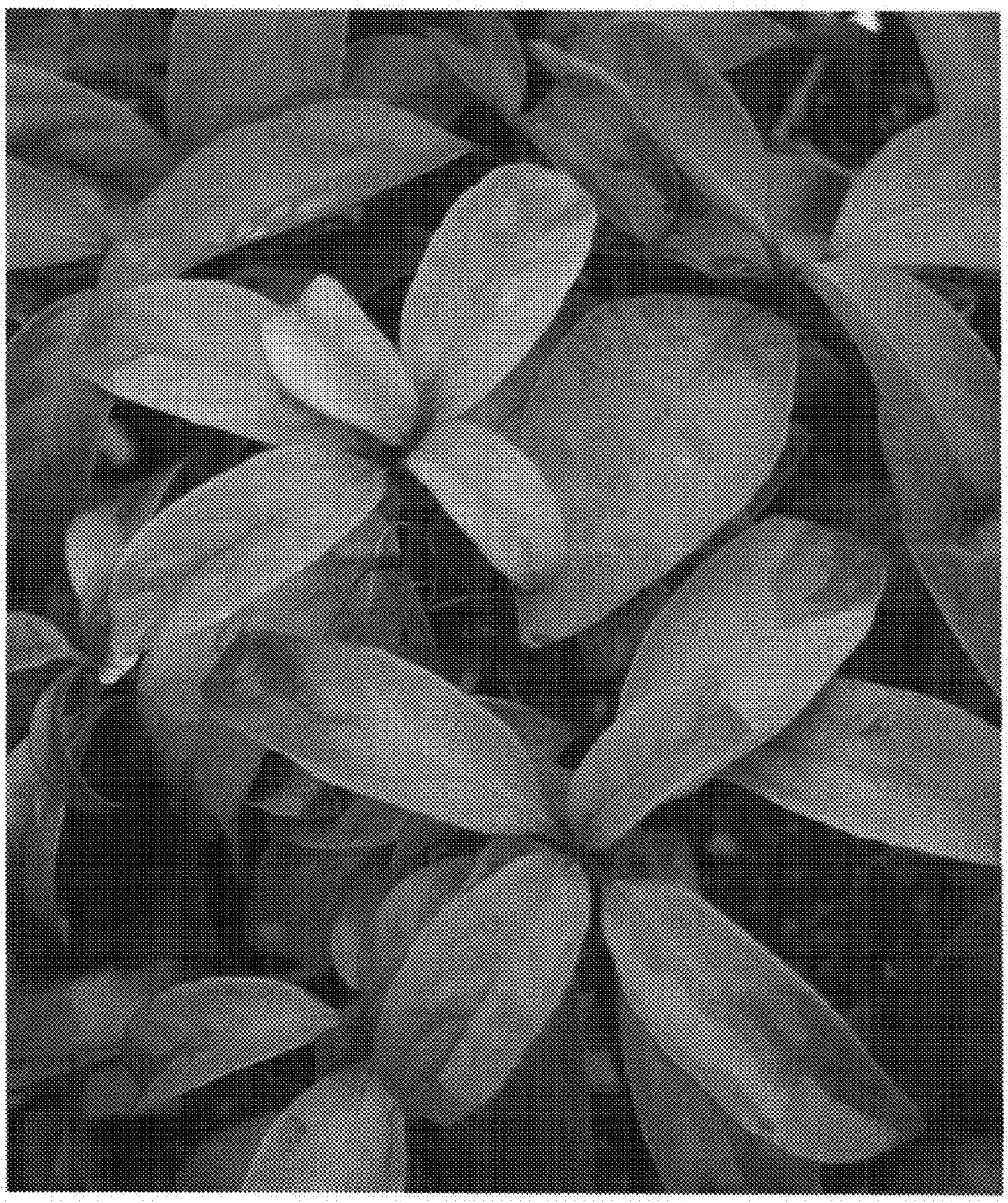

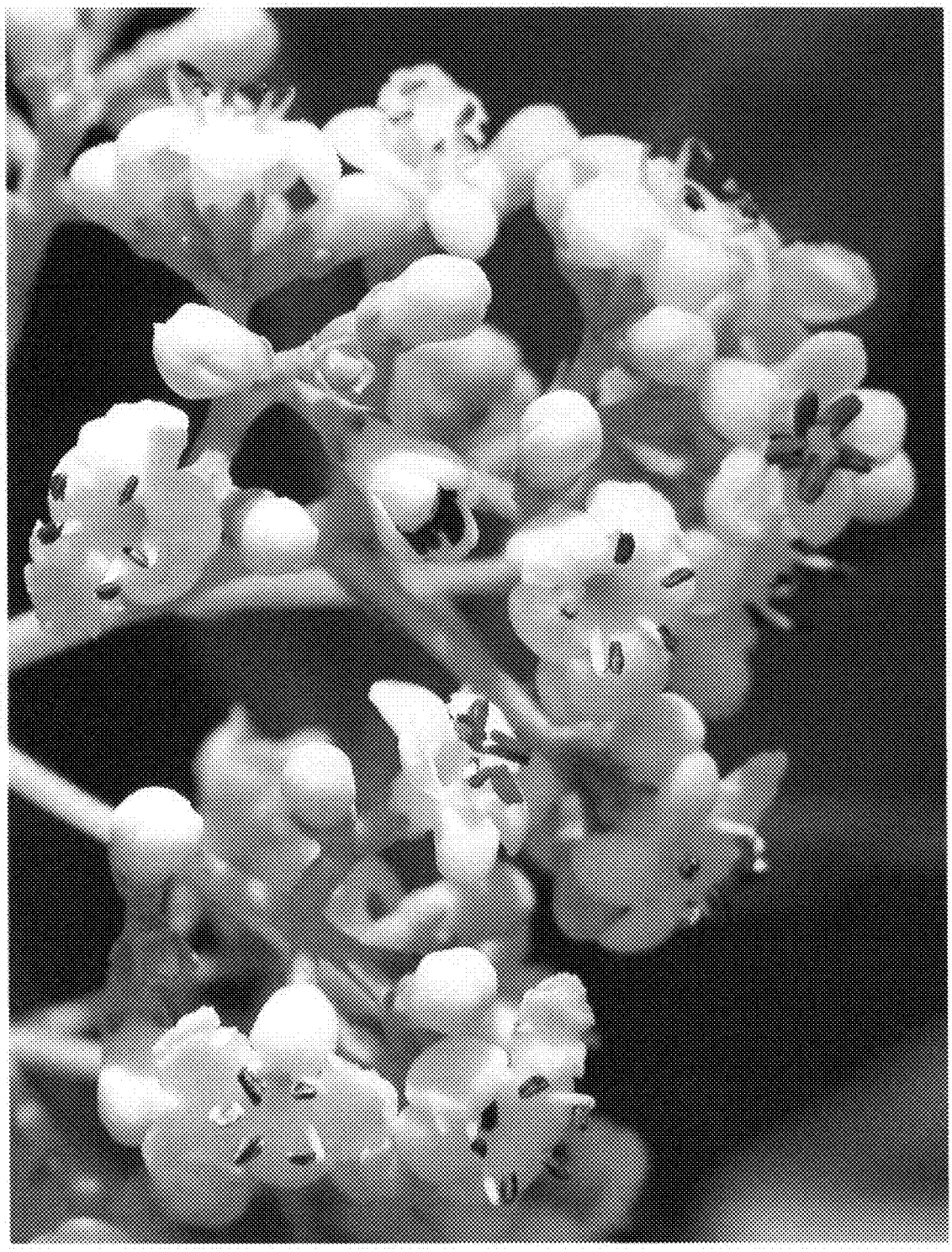

* * * * *